(12) United States Patent
Davis

(10) Patent No.: US 9,908,108 B2
(45) Date of Patent: Mar. 6, 2018

(54) HIGH-SILICA AFX FRAMEWORK TYPE ZEOLITES

(71) Applicant: Chevron U.S.A. Inc., San Ramon, CA (US)

(72) Inventor: Tracy Margaret Davis, Novato, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/498,792

(22) Filed: Apr. 27, 2017

(65) Prior Publication Data

US 2017/0348678 A1 Dec. 7, 2017

Related U.S. Application Data

(60) Provisional application No. 62/346,633, filed on Jun. 7, 2016.

(30) Foreign Application Priority Data

Apr. 25, 2017 (WO) ................ PCT/US2017/029286

(51) Int. Cl.

| | | |
|---|---|---|
| *C01B 39/48* | (2006.01) | |
| *B01J 29/70* | (2006.01) | |
| *B01J 37/04* | (2006.01) | |
| *B01J 37/00* | (2006.01) | |
| *B01J 37/10* | (2006.01) | |
| *C07C 1/20* | (2006.01) | |
| *B01D 53/94* | (2006.01) | |
| *F01N 3/20* | (2006.01) | |

(52) U.S. Cl.
CPC .......... *B01J 29/70* (2013.01); *B01D 53/9418* (2013.01); *B01J 37/0018* (2013.01); *B01J 37/04* (2013.01); *B01J 37/10* (2013.01); *C01B 39/48* (2013.01); *C07C 1/20* (2013.01); *F01N 3/2066* (2013.01); *B01D 2255/2092* (2013.01); *B01D 2255/50* (2013.01); *C07C 2529/70* (2013.01); *F01N 2370/04* (2013.01)

(58) Field of Classification Search
CPC ...... C01B 39/48; B01J 29/70; B01D 53/9418; B01D 2255/50
See application file for complete search history.

(56) References Cited

U.S. PATENT DOCUMENTS

| | | | |
|---|---|---|---|
| 4,508,837 A * | 4/1985 | Zones | ...................... B01J 29/04 423/326 |
| 4,589,976 A * | 5/1986 | Zones | ...................... B01J 29/04 208/111.01 |
| 5,194,235 A * | 3/1993 | Zones | ..................... C01B 39/48 423/704 |
| 8,562,942 B2 * | 10/2013 | Archer | ................. C01B 37/007 423/706 |
| 2016/0096169 A1 * | 4/2016 | Rivas-Cardona | ..... C01B 39/026 423/700 |
| 2016/0137518 A1 | 5/2016 | Rivas-Cardona et al. | |
| 2016/0334732 A1 * | 11/2016 | Okubo | ............... G03G 15/0266 |
| 2017/0136405 A1 * | 5/2017 | Ravikovitch | ...... B01D 53/0462 |
| 2017/0348679 A1 * | 12/2017 | Naraki | .................... B01J 37/30 |

OTHER PUBLICATIONS

Wilson et al, "Synthesis, characterization and structure of SAPO_56, a member of the ABC double-six-ring family of materials with stacking sequence AABBCCBB", Microporous and Mesoporous Materials, 28 (1999) pp. 127-137.*

S.I. Zones and R.A. Van Nordstrand "Further studies on the conversion of Cubic P zeolite to high silica organozeolites" Zeolites 1988, 8, 409-415.

R.F. Lobo, S.I. Zones and R.C. Medrud "Synthesis and Rietveld refinement of the small-pore zeolite SSZ-16" Chem. Mater. 1996, 8, 2409-2411.

R.H. Archer, S.I. Zones and M.E. Davis "Imidazolium structure directing agents in zeolite synthesis: Exploring guest/host relationships in the synthesis of SSZ-70" Micropor. Mesopor. Mater. 2010, 130, 255-265.

* cited by examiner

*Primary Examiner* — David M Brunsman
(74) *Attorney, Agent, or Firm* — Terrence M. Flaherty

(57) ABSTRACT

An AFX framework type zeolite having a $SiO_2/Al_2O_3$ molar ratio of greater than 50 is disclosed. The high-silica AFX framework type zeolite is synthesized from a reaction mixture having high silica and low hydroxide concentrations in the presence of an organic structure directing agent comprising 1,3-bis(1-adamantyl)imidazolium cations.

10 Claims, No Drawings

HIGH-SILICA AFX FRAMEWORK TYPE ZEOLITES

TECHNICAL FIELD

This disclosure relates generally to an AFX framework type zeolite having a $SiO_2/Al_2O_3$ molar ratio of greater 50 to 100, its synthesis, and its use as an adsorbent and a catalyst.

BACKGROUND

Both natural and synthetic molecular sieve materials (e.g., zeolites, aluminophosphates, or mesoporous materials) have been demonstrated to have catalytic properties for various types of hydrocarbon conversion and are utilized in a number of industrial processes. These materials are characterized by ordered, porous crystalline structures that can be determined by X-ray diffraction (XRD). Because the pores of these materials are of molecular dimensions, selective size-exclusive adsorption is possible, hence the name, "molecular sieves."

Molecular sieves are classified by the Structure Commission of the International Zeolite Association according to the rules of the IUPAC Commission on Zeolite Nomenclature. According to this classification, framework type zeolites and other crystalline microporous molecular sieves, for which a structure has been established, are assigned a three letter code and are described in the "*Atlas of Zeolite Framework Types*," Sixth Revised Edition, Elsevier, 2007.

Molecular sieves identified by the International Zeolite Association as having the framework type AFX are known. One example of an AFX framework type material is zeolite SSZ-16.

U.S. Pat. No. 4,508,837 discloses zeolite SSZ-16 and its preparation in the presence of organic nitrogen-containing compound derived from 1,4-di(1-azoniabicyclo[2.2.2]octane) lower alkanes, wherein the lower alkane portion of the organic nitrogen-containing compound has from 3 to 5 carbon atoms.

U.S. Pat. No. 5,194,235 discloses a method for preparing zeolite SSZ-16 using a DABCO-$C_n$-diquat organic structure directing agent where n is 3, 4, or 5. It is reported that the as-prepared SSZ-16 zeolite has a $SiO_2/Al_2O_3$ molar ratio that is typically in a range of 8 to 15.

R. F. Lobo et al. (*Chem. Mater.* 1996, 8, 2409-2411) report that zeolite SSZ-16 can be only synthesized in a restricted range of $SiO_2/Al_2O_3$ molar ratios.

U.S. Pat. No. 8,562,942 discloses the synthesis of an AFX framework type zeolite in the presence of 1,3-bis(1-adamantyl)imidazolium cations at a $SiO_2/Al_2O_3$ molar ratio of 35 and a hydroxide/silica molar ratio of 0.05 for the reaction mixture. At higher $SiO_2/Al_2O_3$ molar ratios (e.g., 50 or 100), materials other than AFX framework type zeolites were produced.

U.S. Patent Application Publication No. 2016/0137518 discloses an aluminosilicate zeolite having at least 90% phase pure AFX framework and a $SiO_2/Al_2O_3$ molar ratio of 12 to 50.

According to the present disclosure, an AFX aluminosilicate zeolite having a $SiO_2/Al_2O_3$ molar ratio of greater than 50 to 100 is disclosed.

SUMMARY

In one aspect, there is provided an AFX framework type zeolite having, in its calcined form, a $SiO_2/Al_2O_3$ molar ratio of greater than 50 to 100.

In another aspect, there is provided an AFX framework type zeolite having, in it as-synthesized and anhydrous form, a composition, in terms of molar ratios, as follows:

|  | Useful | Exemplary |
|---|---|---|
| $SiO_2/Al_2O_3$ | >50 to 100 | >50 to 80 |
| $Q/SiO_2$ | >0 to 0.1 | >0 to 0.1 |
| $M/SiO_2$ | >0 to 0.1 | >0 to 0.1 | wherein Q comprises 1,3-bis(1-adamantyl)imidazolium cations and M is a metal selected from Groups 1 and 2 of the Periodic Table.

In a further aspect, there is provided a method of synthesizing an AFX framework type zeolite having a $SiO_2/Al_2O_3$ molar ratio of greater than 50 to 100, the method comprising: (a) providing a reaction mixture comprising: (1) a source of aluminum comprising a FAU framework type zeolite; (2) a separate source of silicon; (3) a source of at least one metal (M) selected from Groups 1 and 2 of the Periodic Table; (4) a source of 1,3-bis(1-adamantyl)imidazolium cations (Q); (5) hydroxide ions; and (6) water; and (b) subjecting the reaction mixture to crystallization conditions sufficient to form crystals of the AFX framework type zeolite, wherein the reaction mixture has a composition, in terms of molar ratios, as follows:

| | |
|---|---|
| $SiO_2/Al_2O_3$ | >50 to 100 |
| $M/SiO_2$ | 0.05 to 0.25 |
| $Q/SiO_2$ | 0.10 to 0.30 |
| $OH/SiO_2$ | 0.15 to 0.55 |
| $H_2O/SiO_2$ | 15 to 60 |

In yet a further aspect, there is provided a process for converting a feedstock comprising an organic compound to a conversion product which comprises the step of contacting the feedstock with a catalyst at organic compound conversion conditions, the catalyst comprising an active form of the present AFX framework type zeolite.

In still yet a further aspect, there is provided a process for selectively reducing nitrogen oxides ($NO_x$), the process comprising contacting a gas stream containing $NO_x$ with a catalyst comprising an active form of the present AFX framework type zeolite.

DETAILED DESCRIPTION

Introduction

The following terms will be used throughout the specification and will have the following meanings unless otherwise indicated.

The term "zeolite" refers to crystalline aluminosilicate compositions which are microporous and which are formed from corner-sharing $AlO_2$ and $SiO_2$ tetrahedra.

The terms "framework type" is used in the sense described in the "*Atlas of Zeolite Framework Types*," Sixth Revised Edition, Elsevier, 2007.

The term "as-synthesized" is employed herein to refer to a zeolite in its form after crystallization, prior to removal of the organic structure directing agent.

The term "anhydrous" is employed herein to refer to a zeolite substantially devoid of both physically adsorbed and chemically adsorbed water.

As used herein, the numbering scheme for the Periodic Table Groups is as disclosed in *Chem. Eng. News,* 63(5), 27 (1985).

Reaction Mixture

In general, the present AFX framework type zeolite is prepared by: (a) providing a reaction mixture comprising: (1) a source of aluminum comprising a FAU framework type zeolite; (2) a separate source of silicon; (3) a source of at least one metal (M) selected from Groups 1 and 2 of the Periodic Table; (4) a source of 1,3-bis(1-adamantyl)imidazolium cations (Q); (5) hydroxide ions; and (6) water; and (b) subjecting the reaction mixture to crystallization conditions sufficient to form crystals of the AFX framework type zeolite.

The composition of the reaction mixture from which the AFX framework type zeolite is formed, in terms of molar ratios, is identified in Table 1 below:

TABLE 1

| Reactants | Useful | Exemplary |
|---|---|---|
| $SiO_2/Al_2O_3$ | >50 to 100 | 60 to 95 |
| $M/SiO_2$ | 0.05 to 0.25 | 0.05 to 0.10 |
| $Q/SiO_2$ | 0.10 to 0.30 | 0.10 to 0.17 |
| $OH/SiO_2$ | 0.15 to 0.55 | 0.15 to 0.27 |
| $H_2O/SiO_2$ | 15 to 60 | 20 to 50 | wherein compositional variables M and Q are as described herein above.

Suitable FAU framework type zeolites are available, for example, from Zeolyst International (Conshohocken, Pa.) and Tosoh Corporation (Tokyo, Japan).

The FAU framework type zeolite may have a $SiO_2/Al_2O_3$ molar ratio in a range of from 5 to 100 (e.g., 5 to 80, 5 to 60, 5 to 30, 10 to 100, 10 to 80, 10 to 60, or 10 to 30).

Suitable sources of aluminum in addition to the FAU framework type zeolite include hydrated alumina and water-soluble aluminum salts (e.g., aluminum nitrate).

Suitable sources of silicon include colloidal silica, fumed silica, precipitated silica, alkali metal silicates, and tetraalkyl orthosilicates.

Examples of suitable Group 1 or Group 2 metals (M) include sodium, potassium and calcium, with sodium being preferred. The metal (M) is generally present in the reaction mixture as the hydroxide.

The present AFX framework type zeolite is synthesized using an organic structure directing agent comprising 1,3-bis(1-adamantyl)imidazolium cations (Q), represented by the following structure (1):

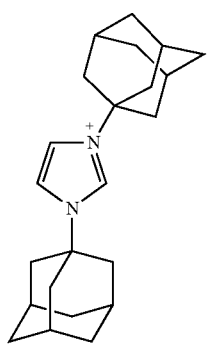

(1)

Suitable sources of Q are the hydroxides, chlorides, bromides, and/or other salts of the quaternary ammonium compound.

The reaction mixture also contains a source of hydroxide ions, for example, a Group 1 metal hydroxide such as sodium hydroxide or potassium hydroxide. Hydroxide can also be present as a counter ion of the organic structure directing agent.

The reaction mixture may also contain seeds of a molecular sieve material, such as zeolite SSZ-16, from a previous synthesis, desirably in an amount of from 0.01 to 10,000 ppm by weight (e.g., from 100 to 5000 ppm by weight) of the reaction mixture.

For each embodiment described herein, the zeolite reaction mixture can be supplied by more than one source. Also, two or more reaction components can be provided by one source.

The reaction mixture can be prepared either batch wise or continuously. Crystal size, morphology and crystallization time of the zeolite described herein can vary with the nature of the reaction mixture and the crystallization conditions.

Crystallization and Post-Synthesis Treatment

Crystallization of the zeolite from the above reaction mixture can be carried out under either static, tumbled or stirred conditions in a suitable reactor vessel, such as for example polypropylene jars or Teflon-lined or stainless steel autoclaves, at a temperature of from 125° C. to 200° C. for a time sufficient for crystallization to occur at the temperature used, e.g., from 5 to 30 days. The crystallization is usually carried out under autogenous pressure.

Once the zeolite crystals have formed, the solid product is recovered from the reaction mixture by standard mechanical separation techniques such as centrifugation or filtration. The crystals are water-washed and then dried to obtain the as-synthesized zeolite crystals. The drying step is typically performed at a temperature of less than 200° C.

As a result of the crystallization process, the recovered crystalline zeolite product contains within its pore structure at least a portion of the organic structure directing agent used in the synthesis.

The as-synthesized zeolite may be subjected to treatment to remove part or all of the organic structure directing agent used in its synthesis. This can be conveniently effected by thermal treatment (calcination) in which the as-synthesized material is heated at a temperature of at least about 370° C. for at least 1 minute and generally not longer than 20 hours. The thermal treatment can be performed at a temperature up to 925° C. While sub-atmospheric pressure can be employed for the thermal treatment, atmospheric pressure is desired for reasons of convenience. Additionally or alternatively, the organic structure directing agent can be removed by treatment with ozone (see, e.g., A. N. Parikh et al., *Micropor. Mesopor. Mater.* 2004, 76, 17-22). The organic-free product, especially in its metal, hydrogen and ammonium forms, is particularly useful in the catalysis of certain organic (e.g., hydrocarbon) conversion reactions. In the present disclosure, the organic-free zeolite in its hydrogen form is referred to as "active form" of the zeolite, with or without metal function present, such as Pt or Pd.

To the extent desired, extra-framework Group 1 or 2 metal cations in the present AFX framework type zeolite may be replaced in accordance with techniques well known in the art by ion exchange with other cations. Suitable replacing cations include metal ions, hydrogen ions, hydrogen precursor ions (e.g., ammonium ions), and combinations thereof. Preferred replacing cations are those which tailor the catalytic activity for certain chemical conversion reactions. Particularly preferred replacing cations include hydrogen, rare earth metals and metals of Groups 2 to 15 of the Periodic Table.

When used as a catalyst, it may be desirable to incorporate the present AFX framework type zeolite with another material resistant to the temperatures and other conditions employed in chemical conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the present AFX framework type zeolite (i.e., combined therewith or present during synthesis of the new crystal), which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays (e.g., bentonite and kaolin) to improve the crush strength of the catalyst under commercial operating conditions. These materials, (i.e., clays, oxides, etc.) function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the present AFX framework type zeolite include the montmorillonite and kaolin family, which families include the sub-bentonites, and the kaolins commonly known as Dixie, McNamee, Ga. and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present AFX framework type zeolite also include inorganic oxides, such as silica, zirconia, titania, magnesia, beryllia, alumina, and mixtures thereof.

In addition to the foregoing materials, the present AFX framework type zeolite can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of the present AFX framework type zeolite and inorganic oxide matrix may vary widely, with the AFX framework type zeolite content ranging from 1 to 90 wt. % (e.g., 2 to 80 wt. %) of the composite.

Characterization of the Zeolite

In its as-synthesized and anhydrous form, the present AFX framework type zeolite has a chemical composition, in terms of molar ratios, as described in Table 2 below.

TABLE 2

|  | Useful | Exemplary |
|---|---|---|
| $SiO_2/Al_2O_3$ | >50 to 100 | >50 to 80 |
| $Q/SiO_2$ | >0 to 0.1 | >0 to 0.1 |
| $M/SiO_2$ | >0 to 0.1 | >0 to 0.1 | wherein Q comprises 1,3-bis(1-adamantyl)imidazolium cations and M is a metal selected from Groups 1 and 2 of the Periodic Table.

In some embodiments, the present AFX framework type zeolite has, in its as-synthesized and anhydrous form, a $SiO_2/Al_2O_3$ molar ratio in a range of greater than 50 to 90 (e.g., >50 to 70, 52 to 90, 52 to 80, 52 to 70, 53 to 90, 53 to 80, 53 to 70, 55 to 90, 55 to 80, or 55 to 70).

It should be noted that the as-synthesized form of the present AFX framework type zeolite may have molar ratios different from the molar ratios of reactants of the reaction mixture used to prepare the as-synthesized form. This result may occur due to incomplete incorporation of 100% of the reactants of the reaction mixture into the crystals formed (from the reaction mixture).

In its calcined from, the present AFX framework type zeolite has a chemical composition comprising the following molar relationship:

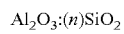

$Al_2O_3:(n)SiO_2$ wherein n has a value from of greater than 50 to 100 (e.g., >50 to 90, >50 to 80, >50 to 70, 52 to 100, 52 to 90, 52 to 80, 52 to 70, 53 to 100, 53 to 90, 53 to 80, 53 to 70, 55 to 100, 55 to 90, 55 to 80, or 55 to 70).

The present high-silica AFX framework type zeolite is characterized by powder X-ray diffraction. Powder XRD patterns representative of AFX framework type zeolites can be referenced in the "*Collection of Simulated XRD Powder Patterns for Molecular Sieves*," Fifth Revised Edition, Elsevier, 2007. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can result from variations in the organic compound used in the preparation. Calcination can also cause minor shifts in the X-ray diffraction pattern. Notwithstanding these minor pertubations, the basic crystal structure remains unchanged.

Using the methods described herein, it is possible to synthesize high-silica AFX framework type zeolites substantially free of non-AFX material. The term "substantially free of non-AFX material" used herein means that the present AFX framework type zeolite contains less than 5 wt. % (e.g., less than 2.5 wt. %, less than 1 wt. %, or no measurable amount) of non-AFX material, as determined by conventional XRD techniques. Examples of such non-AFX materials include amorphous material, unreacted FAU framework type zeolite and CHA framework type zeolite. The non-AFX material may co-crystallize with the AFX material or mix with the AFX material.

Adsorption and Catalysis

The present AFX framework type zeolite can be used as an adsorbent. For example, it can be used as a selective adsorbent in separating a first component (e.g., $CO_2$) from a gaseous mixture comprising the first component and an additional second component (e.g., methane).

The present AFX framework type zeolite can be used to catalyze a wide variety of chemical conversion processes, particularly organic compound (e.g., hydrocarbon) conversion processes. Examples of chemical conversion processes which are effectively catalyzed by this material, by itself or in combination with one or more other catalytically active substances including other crystalline catalysts, include those requiring a catalyst with acid activity.

The present AFX framework type zeolite may be suitable for use as a catalyst in the conversion of oxygenates to one or more olefins, particularly ethylene and propylene. The term "oxygenates" is employed herein to include to aliphatic alcohols, ethers, carbonyl compounds (aldehydes, ketones, carboxylic acids, carbonates, and the like), and also compounds containing hetero-atoms, such as, halides, mercaptans, sulfides, amines, and combinations thereof. The aliphatic moiety will normally contain from 1 to 10 carbon atoms (e.g., 1 to 4 carbon atoms).

Representative oxygenates include lower straight chain or branched aliphatic alcohols, their unsaturated counterparts, and their nitrogen, halogen and sulfur analogs. Particularly suitable oxygenate compounds are methanol, dimethyl ether, or combinations thereof, especially methanol.

In the present oxygenate conversion process, a feedstock comprising an organic oxygenate, optionally with one or more diluents, is contacted in the vapor phase in a reaction zone with a catalyst comprising the present zeolite at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or zeolite catalyst composition and is typically used to reduce the concentration of the oxygenate in the feedstock. Suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. Particularly suitable diluents are water and nitrogen, with water being especially preferred. Diluent(s) may comprise from 1 to 99 mole % of the total feed mixture.

The temperature employed in the oxygenate conversion process may vary over a wide range, such as from 200° C. to 1000° C. (e.g., 250° C. to 800° C., 300° C. to 650° C., or 400° C. to 600° C.).

Light olefin products will form, although not necessarily in optimum amounts, at a wide range of pressures, including autogenous pressures and pressures in the range of from 0.1 kPa to 10 MPa (e.g., 7 kPa to 5 MPa, or 50 kPa to 1 MPa). The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of zeolite catalyst (excluding inerts and/or fillers). The WHSV generally should be in the range of from 0.01 to 500 h$^{-1}$ (e.g., 0.5 to 300 h$^{-1}$, or 1 to 200 h$^{-1}$).

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

The present AFX framework type zeolite may be used in a catalytic process involving the conversion of at least one compound comprising at least one nitrogen-oxygen bond. Particularly suitable are processes wherein the present zeolite is used as a catalyst and/or catalyst support in a selective catalytic reduction (SCR) process. In this process, a gaseous stream comprising nitrogen oxides (NO$_x$) is selectively reduced in the presence of a reductant and a catalyst comprising the present AFX framework type zeolite. The nitrogen oxides (principally NO and NO$_2$) are reduced to N$_2$ while the reductant is oxidized. When ammonia is the reductant, N$_2$ is also an oxidation product. Ideally, the only reaction products are water and N$_2$, although some NH$_3$ is usually oxidized with air to NO or N$_2$O.

To promote the catalytic activity, one more transition metals may be incorporated into the zeolite support. Any suitable transition metal may be selected. Transition metals particularly effective for use during selective catalytic reduction include one or more of Cr, Mn, Fe, Co, Ce, Ni, Cu, Mo, Ru, Rh, Pd, Ag, Re, Ir, and Pt. In one embodiment, the transition metal is selected from Fe and Cu. In an exemplary embodiment, the transition metal is Cu. Any suitable and effective amount of transition metal may be used in the catalyst. The total amount of the transition metal(s) that may be included in the zeolite may be from 0.01 to 10 wt. % (e.g., 0.5 to 5 wt. %, or 1 to 2.5 wt. %) based on the total weight of the zeolite support.

The zeolite catalyst for use in the reduction of nitrogen oxides may be coated on a suitable substrate monolith or can be formed as extruded-type catalysts, but is preferably used in a catalyst coating. In one embodiment, the zeolite catalyst is coated on a flow-through monolith substrate (i.e., a honeycomb monolithic catalyst support structure with many small, parallel channels running axially through the entire part) or filter monolith substrate, such as a wall-flow filter, etc. The zeolite catalyst for use herein may be coated (e.g., as a washcoat component) on a suitable monolith substrate, such as a metal or ceramic flow through monolith substrate or a filtering substrate, such as a wall-flow filter or sintered metal or partial filter. Alternatively, the zeolite may be synthesized directly onto the substrate and/or may be formed into an extruded-type flow through catalyst.

The gaseous stream comprising nitrogen oxides may contain one or more of NO, NO$_2$, and N$_2$O in addition to other non-NO$_x$ gases such as N$_2$, O$_2$, CO, CO$_2$, SO$_2$, HCl and H$_2$O. The gaseous stream may contain from 1 to 10,000 ppm (e.g., 10 to 1,000 ppm, or 50 to 500 ppm) of NO.

The nitrogen oxides which are reduced using a catalyst containing the present AFX framework type zeolite may be obtained by any process (e.g., as a waste gas stream). In one embodiment, the gaseous stream containing NO$_x$ is an exhaust gas from an internal combustion engine.

The reductant can be a nitrogen compound or a short-chain (C$_1$ to C$_8$) hydrocarbon. Preferably, the reductant is a nitrogen compound. Suitable nitrogen compounds include ammonia, hydrazine, and ammonia precursors (e.g., urea, ammonium carbonate, ammonium carbamate, ammonium hydrogen carbonate, and ammonium formate).

The gaseous stream comprising nitrogen oxides can contact the catalyst at a gas hourly space velocity of from 5000 to 500,000 h$^{-1}$ (e.g., 10,000 to 200,000 h$^{-1}$).

The reduction of nitrogen oxides may be carried out at a temperature within the range of 100° C. to 650° C. (e.g., 250° C. to 600° C.).

The reduction of nitrogen oxides may be carried out in the presence of oxygen or in the absence of oxygen.

EXAMPLES

The following illustrative examples are intended to be non-limiting.

Example 1

Zeolite SSZ-16 was prepared according the procedure described in U.S. Pat. No. 4,508,837. The source of silicon was sodium silicate, the source of aluminum was aluminum sulfate, and the structure directing agent was 1,4-di(1-azoniabicyclo[2.2.2]octane)butyl dibromide.

The powder XRD of the resulting product was characteristic for SSZ-16.

The as-synthesized product had a $SiO_2/Al_2O_3$ molar ratio of 12, as determined by ICP elemental analysis.

Example 2

Zeolite SSZ-16 was prepared according the procedure described in U.S. Pat. No. 5,194,235. A PTFE cup was charged with 1.75 g of a sodium silicate solution, 0.18 g of LZ-210 zeolite ($NH_4$-USY, $SiO_2/Al_2O_3$ molar ratio=15), 3.77 g of 1N NaOH, 1.56 g of deionized water, and 0.49 g of 1,1'-(butane-1,4-diyl)bis[4-aza-1-azoniabicyclo[2.2.2]octane] dibromide (DABCO-$C_4$-DABCO dibromide). The mixture was stirred with a spatula to homogenize. The final composition of the reaction mixture, in terms of molar ratios, was as follows:

| | |
|---|---|
| $SiO_2/Al_2O_3$ | 72 |
| $Q/SiO_2$ | 0.15 |
| $NaOH/SiO_2$ | 0.9 |
| $H_2O/SiO_2$ | 35 |

The PTFE cup was capped and sealed in a stainless steel autoclave. The autoclave was then fixed in a rotating spit (43 rpm) within an oven heated at 140° C. for 14 days. The solid products were recovered from the cooled reactor by filtration and washed with deionized water. The recovered solids were then allowed to dry in an oven overnight at 95° C.

The powder XRD of the resulting product was characteristic for SSZ-16.

The as-synthesized product had a $SiO_2/Al_2O_3$ molar ratio of 9.5, as determined by ICP elemental analysis.

Example 3

Example 2 was repeated except that the final composition of the reaction mixture, in terms of molar ratios, was as follows:

| | |
|---|---|
| $SiO_2/Al_2O_3$ | 35 |
| $Q/SiO_2$ | 0.15 |
| $NaOH/SiO_2$ | 1.0 |
| $H_2O/SiO_2$ | 33.8 |

The powder XRD pattern of the resulting product was characteristic for SSZ-16.

The as-synthesized product had a $SiO_2/Al_2O_3$ molar ratio of 7.1, as determined by ICP elemental analysis.

Example 4

An AFX framework type zeolite was prepared was prepared according the procedure described in U.S. Pat. No. 8,562,942. A PTFE cup was charged with 0.19 g of CBV100 Na—Y zeolite (Zeolyst International, $SiO_2/Al_2O_3$ molar ratio=5.1), 1 g of 1N NaOH, 3.47 g of an aqueous solution of 1,3-bis(1-adamantyl)imidazolium hydroxide (0.58 mmole OH/g solution), and 1.61 g of water. Then, 0.62 g of CAB-O-SIL® M-5 fumed silica (Cabot Corporation) was added. The mixture was stirred with a spatula to homogenize. The final composition of the reaction mixture, in terms of molar ratios, was as follows:

| | |
|---|---|
| $SiO_2/Al_2O_3$ | 34 |
| $Q/SiO_2$ | 0.20 |
| $NaOH/SiO_2$ | 0.158 |
| $H_2O/SiO_2$ | 30 |

The PTFE cup was capped and sealed in a stainless steel autoclave. The autoclave was then fixed in a rotating spit (43 rpm) within an oven heated at 150° C. for 21 days. The solid products were recovered from the cooled reactor by filtration and washed with deionized water. The recovered solids were then allowed to dry in an oven overnight at 95° C.

The powder XRD of the resulting product was characteristic for AFX framework type materials.

The as-synthesized product had a $SiO_2/Al_2O_3$ molar ratio of 28, as determined by ICP elemental analysis.

Example 5

A PTFE cup was charged with 0.62 g of CAB-O-SIL® M-5 fumed silica (Cabot Corporation), 0.18 g of LZ-210 zeolite, 1.0 g of 1N NaOH, and 3.47 g of an aqueous solution of 1,3-bis(1-adamantyl)imidazolium hydroxide (0.58 mmol OH/g solution). The mixture was stirred with a spatula to homogenize. The final composition of the reaction mixture, in terms of molar ratios, was as follows:

| | |
|---|---|
| $SiO_2/Al_2O_3$ | 90 |
| $Q/SiO_2$ | 0.17 |
| $NaOH/SiO_2$ | 0.08 |
| $H_2O/SiO_2$ | 25 |

The PTFE cup was capped and sealed in a stainless steel autoclave. The autoclave was then fixed in a rotating spit (43 rpm) within an oven heated at 150° C. for 21 days. The solid products were recovered from the cooled reactor by filtration and washed with deionized water. The recovered solids were then allowed to dry in an oven overnight at 95° C.

The powder XRD of the resulting product was characteristic for AFX framework type materials.

The as-synthesized product had a $SiO_2/Al_2O_3$ molar ratio of 66, as determined by ICP elemental analysis.

Example 6

A PTFE cup was charged with 0.62 g of CAB-O-SIL® M-5 fumed silica (Cabot Corporation), 0.25 g of LZ-210 zeolite, 1.2 g of 1N NaOH, and 3.47 g of an aqueous solution of 1,3-bis(1-adamantyl)imidazolium hydroxide (0.58 mmol OH/g solution). The mixture was stirred with a spatula to homogenize. The final composition of the reaction mixture, in terms of molar ratios, was as follows:

| | |
|---|---|
| SiO$_2$/Al$_2$O$_3$ | 70 |
| Q/SiO$_2$ | 0.16 |
| NaOH/SiO$_2$ | 0.09 |
| H$_2$O/SiO$_2$ | 24 |

The PTFE cup was capped and sealed in a stainless steel autoclave. The autoclave was then fixed in a rotating spit (43 rpm) within an oven heated at 150° C. for 21 days. The solid products were recovered from the cooled reactor by filtration and washed with deionized water. The recovered solids were then allowed to dry in an oven overnight at 95° C.

The powder XRD of the resulting product was characteristic for AFX framework type materials.

The as-synthesized product had a SiO$_2$/Al$_2$O$_3$ molar ratio of 53, as determined by ICP elemental analysis.

The invention claimed is:

1. An AFX framework type zeolite having, it its calcined form, a composition comprising the molar relationship:

$$Al_2O_3:(n)SiO_2$$

wherein n has a value of greater than 50 to 100.

2. The AFX framework type zeolite of claim 1, wherein n has a value of greater than 50 to 80.

3. The AFX framework type zeolite of claim 1, wherein n has a value of 52 to 70.

4. A process for converting a feedstock comprising an organic compound to a conversion product which comprises the step of contacting the feedstock with a catalyst, at organic compound conversion conditions, the catalyst comprising an active form of the AFX framework type zeolite of claim 1.

5. A process for selectively reducing nitrogen oxides (NO$_x$), the process comprising contacting a gas stream containing NO$_x$ with a catalyst comprising the zeolite of claim 1.

6. An AFX framework type zeolite having, in it as-synthesized and anhydrous form, a composition, in terms of molar ratios, as follows:

| | |
|---|---|
| SiO2/Al$_2$O$_3$ | >50 to 100 |
| Q/SiO$_2$ | >0 to 0.1 |
| M/SiO$_2$ | >0 to 0.1 | wherein Q comprises 1,3-bis(1-adamantyl)imidazolium cations and M is a metal selected from Groups 1 and 2 of the Periodic Table.

7. The AFX framework type zeolite of claim 6, wherein the SiO$_2$/Al$_2$O$_3$ molar ratio is in a range of greater than 50 to 80.

8. The AFX framework type zeolite of claim 6, wherein the SiO$_2$/Al$_2$O$_3$ molar ratio is in a range of from 52 to 70.

9. A method of synthesizing the AFX framework type zeolite of claim 6, the method comprising:
(a) providing a reaction mixture comprising:
(1) a source of aluminum comprising a FAU framework type zeolite;
(2) a separate source of silicon;
(3) a source of at least one metal (M) selected from Groups 1 and 2 of the Periodic Table;
(4) a source of 1,3-bis(1-adamantyl)imidazolium cations (Q);
(5) hydroxide ions; and
(6) water; and
(b) subjecting the reaction mixture to crystallization conditions sufficient to form crystals of the AFX framework type zeolite,
wherein the reaction mixture has a composition, in terms of molar ratios, as follows:

| | |
|---|---|
| SiO$_2$/Al$_2$O$_3$ | >50 to 100 |
| M/SiO$_2$ | 0.05 to 0.25 |
| Q/SiO$_2$ | 0.10 to 0.30 |
| OH/SiO$_2$ | 0.15 to 0.55 |
| H$_2$O/SiO$_2$ | 15 to 60. |

10. The method of claim 9, wherein the crystallization conditions include a temperature of from 125° C. to 200° C.

* * * * *